United States Patent [19]

Ries et al.

[11] 4,206,511
[45] Jun. 3, 1980

[54] LOCATING A WELDING SEAM

[75] Inventors: Karl Ries; Dieter Kaiser; Wolfgang Terschüren, all of Mülheim, Fed. Rep. of Germany

[73] Assignee: Mannesmann Aktiengesellschaft, Düsseldorf, Fed. Rep. of Germany

[21] Appl. No.: 906,435

[22] Filed: May 17, 1978

[30] Foreign Application Priority Data

May 18, 1977 [DE] Fed. Rep. of Germany ....... 2722961

[51] Int. Cl.² .............................................. G01S 9/68
[52] U.S. Cl. ..................................... 367/96; 367/104; 367/117; 73/625
[58] Field of Search ................. 340/1 R; 73/597, 598, 73/606, 625, 641

[56] References Cited

U.S. PATENT DOCUMENTS

| | | | |
|---|---|---|---|
| 3,149,561 | 9/1964 | Lancaster | 340/1 R X |
| 3,313,146 | 4/1967 | Krautkramer | 73/625 |
| 3,651,687 | 3/1972 | Dory | 340/1 R X |
| 3,944,963 | 3/1976 | Hively | 340/1 R |

Primary Examiner—Richard A. Farley
Attorney, Agent, or Firm—Smyth, Pavitt, Siegemund, Jones & Martella

[57] ABSTRACT

The welding seam of a pipe is located by means of ultrasonic transducers and echo pulses responding particularly to rather minute distance differences on account of the convex contour of the seam and its elevation above the continued contour of the unmodified parts being welded together. A two or a three transducer configuration is used.

3 Claims, 2 Drawing Figures

LOCATING A WELDING SEAM

BACKGROUND OF THE INVENTION

The present invention relates to locating a welding seam for purposes of centering ultrasonic test equipment which non-destructively examines e.g. a submerged arc welded seam of pipes.

Ultrasonic test equipment is, for example, particularly positioned in a test stand, and the test object such as a pipe is passed past the equipment. Proper testing requires that the equipment and here particularly the individual ultrasonic test heads and transducers have a well defined position in relation to the seam. Moreover, that position should be related to the center line of the seam.

Locating the welding seam can be carried out for example inductively by using the geometric irregularities in the material next to the welding seam. Moreover, the seam itself must have a particular height above the surface contour of the parts being welded (e.g. the cylinder as defined by the outer surface vs. a pipe). Such a elevation must exceed 1 millimeter. For lower heights or elevations, the weld center may escape detection. Also, inductive measurement is rather temperature sensitive so that additional errors must be expected on that account.

DESCRIPTION OF THE INVENTION

It is an object of the present invention to provide a new and improved method and system for locating the welding seams in relation to seam test equipment along which the test object having the seam passes during testing, for purposes of tracking the seam. The method is to be rather insensitive to temperature variations, even relatively large ones. Moreover, the method must be suitable even for locating welds of rather low height.

In accordance with the preferred embodiment of the invention, it is suggested to use a plurality of pulse echo ultrasonic transducers being laterally spaced apart, adjacent to the welding seam and measuring the transit time of surface echos. These transit times bear a specific relation to each other which varies upon lateral displacement of the test object. In a two transducer configuration one places these transducers symmetrical to the center of the seam; in a three transducer configuration one transducer is to be above the center, the two others alongside the seam adjacent to surface portions off the seam. The sensitivity of this method permits ready response to deflections of the seam, even if its surface is rather shallow; small deviations from the unmodified surface contour suffice to locate the seam and its center.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 shows a test object such as a portion of a large, seam welded pipe. The welding seam 2 and adjacent regions constitute the part to be examined as to flaws and defects by means of an ultrasonic test equipment, disposed on a carriage or table 6. The test equipment including mounting structure is shown in greater detail in copending application of some of us and common assignee, Ser. No. 767,353, filed Feb. 10, 1977. The device presently described can be used as seam locator and follower control in that equipment.

Figure 1:
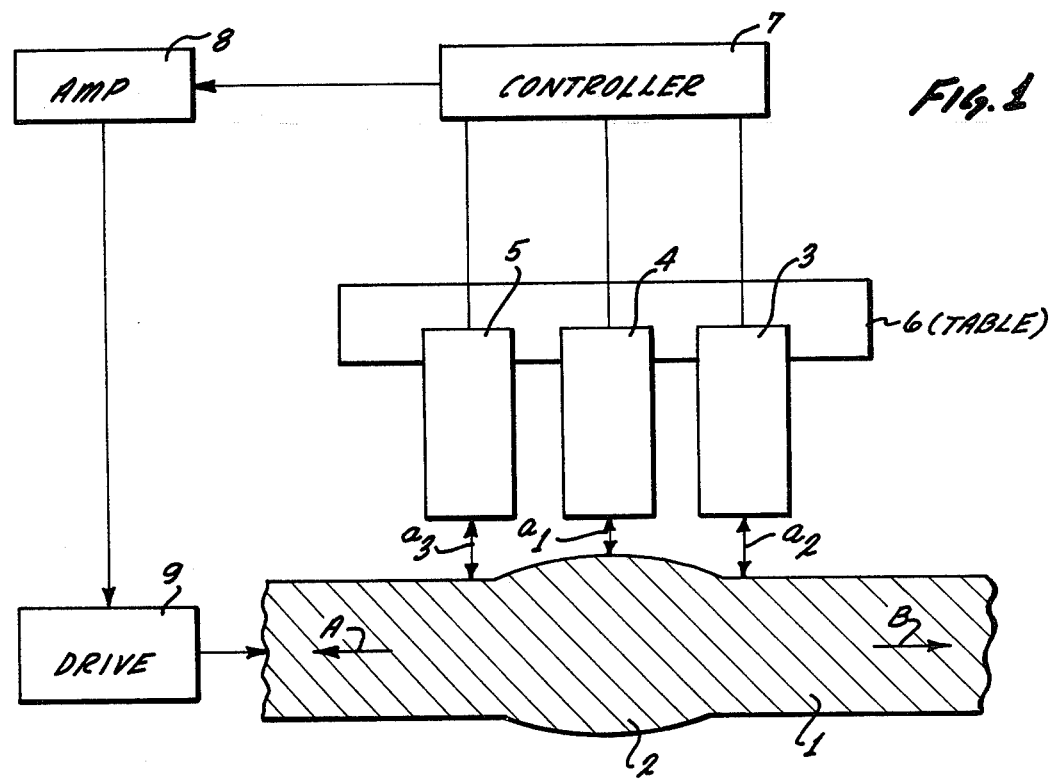
FIG. 1 is a schematic view and block diagram of a system for practicing the inventive method in accordance with the preferred embodiment under utilization of three transducers.

It appears that the holder, table or carriage 6 is to be centered as far as the test equipment is concerned, with respect to the welding seam 2 passing the test equipment in a direction transversely to the drawing. It should be noted that actually the test equipment and table may better be placed underneath in that the seam is in the six o'clock position for testing.

In order to center the test equipment three ultrasonic transducers 3, 4 and 5 are mounted on the table 6. They are not necessarily a part of the test equipment though there is no reason why these or some of these transducers should not be used additionally to perform test tasks. They all may be mounted in a common water tank or water may otherwise be provided between the transducing front surface of each transducer and the test object 1,2. It may well be advisable to subject the water to temperature control which is very beneficial for making the method temperature insensitive.

The front surfaces of the transducers may be disposed in a common plane. If the test object is a pipe, the front surfaces may actually be disposed on a (geometric) cylinder surface which is concentric with the pipe. However, some offset can be taken care of by calibration of the equipment including the responses as derived in a manner to be described below.

The three transducers 3, 4 and 5 are laterally spaced, but in a common axial plane (e.g. the plane of the drawing) and by fixed distances selected so that the two outer transducers 3 and 5 are spaced by more than the width of the seam 2 while the third transducer 4 is placed in the middle between the two others. As a consequence, transducers 3 and 5 face pipe surface portions outside the seam when the transducer 4 is centered above the center line of the seam. This is the correct position; that is to say the test equipment on table 6 has the desired and required position relative to seam 2 as long as transducer 4 is centered above the seam as illustrated.

The presence of the desired position as well as following and tracking this position is maintained as follows. The transducing surfaces are spaced from the test object by distances which are propagative paths for ultrasonic waves through the water. These distances are denoted a1, a2 and a3 as shown in the drawing. Ideally, a2=a3, whenever the transducers 3 and 5 face test object surface positions outside of the seam. However, for reasons below this equality in distance is not mandatory, i.e. there may be some misalignment or offset, a2−a3≠0. It is convenient, however, to select the distance a1 of transducer 4 from the peak of the welding seam to be smaller than a2 or a3, and it will be assumed that this is the case, though the possibility of a fixed offset is also permissible and can be eliminated through signal processing.

Those distances a1, a2, a3 are translatable into transit times. That is to say an ultrasonic pulse transmitted by the transducers will be returned as an echo by the water-test object interface, and that return is considerably earlier for transducer 4 than for transducers 3 and 5. It was found that for ultrasonic waves and pulses as they are commonly used for the insepection itself, the distance measured in terms of transit time is very sensitive, i.e. a fraction of a millimeter, so that even in the case of welding seam peak heights of less than a millimeter above the cylinder surface of the pipe itself (i.e. the undisturbed test object surface) one will still be able to very accurately locate the peak in terms of a minimum distance, minimum transit time of the distance measure echo.

A controller 7 for the system provides energizing pulses to the three transducers 3, 7, 5, conceivably concurrently or in sequence as serial operation may require less hardware. Each such pulse starts e.g. a counter in controller 7 to be stopped by the respective return echo when responded to by the launching transducer. The count state meters the respective transit time so that for each shot or each cycle the three distances a1, a2 and a3 are metered.

In the correct position, a1 is at a minimum by definition, but one can also see that a2−a1 and a3−a1 are at a maximum. This remains true irrespective of any offset i.e. irrespective whether or not the transducers are in fact located on a common cylinder. Should the test object and particularly the seam be displaced for any reason and relative to the test equipment on table 6 and in the direction of arrow B, a1 will increase, a2 will decrease and a3 will stay the same. Accordingly, difference a2−a1, will decrease at a steeper slope on a different value vs. the deflection curve than a3−a1 decreases because a2 and a1 both change and in opposite directions, while a3 stays constant. If the seam center is located about half way between transducers 3 and 4, a2−a1 is zero, i.e. changes sign. For a further deflection a2−a1 will reach a negative maximum, and upon still further displacement a1, a2 and a3 will all be about equal; the seam is outside of the detector range.

It can thus be seen that for a considerable range of deflection one can use the sum of the differences (a2−a1) and (a3−a1) as an error signal for purposes of follow up control but on an inverse scale: That sum has a maximum for the correct position and is zero when all three transducers are off the seam. However, if one employs simple on-off control for seam tracking, one may not need this representation. The sign of the difference of the differences gives the direction of the deflection as (a3−a1)>(a2−a1) for that range.

This, however, is strictly true if there is no offset or misalignment. Otherwise, these values have to be corrected by the requisite offset values representing the deviation of the positions of the transducers from a common cylinder. Calibration in transit times particularly when all three transducers face the unmodified cylindrical pipe surface can readily produce the requisite offsets.

The thus modified or present difference of the differences represents the direction of needed correction and may suffice in simple on-off control to turn on a drive 9 for moving the test object back in the direction of arrow A. It should be noted that algebraically an error signal could be formed from the a2 and a3 values along. However, at monitoring, i.e. detecting the center position of the seam is needed to obtain the error signal from at least two oppositely varying distance values. This permits discrimination against e.g. local width changes in the seam which may cause one or the other of the distances a2, a3 to become shorter, through the test object or the equipment has not left the position of mutual alignment. Thus the corrected control should be made dependent upon a change of both difference values a2−a1; a3−a1, before a corrective step be taken. The controller 7, therefor, processes the transit times as ascertained for each measuring cycle to decide whether or not a corrective step is necessary. The controller may well be designed to require several consistent transit times measuring results in several sequential cycles to present unnecessary and undesirable jitter in the control.

In the case of a true error, the controller 7 furnishes an error signal to an amplifyer 8 to operate the drive 9. In the case of a pipe as a test object, drive 9 will turn that pipe on its axis to obtain a corrective displacement in the direction of arrow A. Alternatively and in addition, the table 6 may be moved in direction of arrow B. The control operation may be stopped for example if the difference of the differences (a3−a1) and (a2−a1) tends to change sign. This may lead to a control in the opposite direction if not stopped.

One could also use a1 alone as an indication when to stop corrections, as its value is at a minimum in the correct position. The same is true when the sum of the differences reaches maximum value. However, both indications could lead inherently to a dithering type of control, causing the transducer and the test object to slightly oscillate around the center position. Whenever the seam is deflected in the direction of arrow A, the two measured values a1 and a3 change in opposite direction while a2 remains constant. In this case now, a2−a1>a3−a1 but the sum of the differences is again indicative of the degree of displacement (until a3−a1 reaches its negative maximum.)

Figure 2:
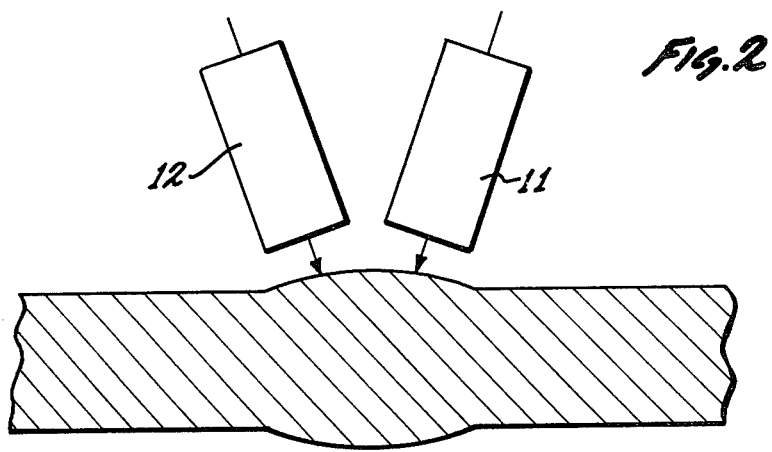
FIG. 2 is a modification of the system shown in FIG. 1, using but two transducers.

As far as FIG. 2 is concerned, this particular seam locating device uses two transducers 11 and 12. In the normal position they are symmetrically arranged to the seam center, and they are disposed at a slight angle commensurate with the slope of the seam for reasons of gain of the return echo. The echo transit times in this instance simply vary in opposite directions from e.g. initially adjusted equal values, whenever the test object deflects. The transit time difference is about proportionate to the deflection and the sign of the difference indicates the direction. However, one can see that the range of control is smaller in that a deflective position of the test object when both transducers face non-seam portions of the object's surface is smaller than in the case of FIG. 1. However, the control as per FIG. 2 may suffice if the dynamic conditions of feedback and follow up are sufficiently fast.

Either one of the two systems may also be used to find the seam in the first place. A pipe may enter the test stand in a rather arbitrary orientation as to its seam. Most likely the seam will not be in the range of either of the detectors. Thus, the transit times and distances measured in these cases will be equal (or differ only by any misalignment or offset). In the case of FIG. 1 this is established by finding both differences (a2−a1; a3−a1) to be zero (subject to misalignment offset). In the case of FIG. 2 the difference in transit times is likewise zero, but that is not sufficient an indication. These transit times have also a particular value which is relatively large. A better indicator is that the difference in transit times does not vary as the pipe rotates.

Finding the seam results from detection of non-zero transit time differences in that the transit time of the transducer facing the oncoming rotation of the pipe is shortened first and the seam finding is completed when the center position as defined above is detected.

The invention is not limited to the embodiments described above but all changes and modifications thereof not constituting departures from the spirit and scope of the invention are intended to be included.

What is claimed is:

1. Method of locating and tracking the welding seam of a test object facing ultrasonic test equipment comprising:

positioning a plurality of laterally spaced ultrasonic transducers adjacent to the seams, but in spaced apart relation thereto, there being relative movement in longitudinal direction as between the transducers and the seam;

causing the transducers to emit pulses; detecting the instants of occurrence of the echos for measuring the respective distances between the transducers and the test object on the basis of transit times for these echos; determining transit time differences of the echos as received respectively by the transducers and providing a representation of the location of the seam in relation to the transducers; and providing a supplemental lateral shift as between the test equipment and said test object to center the test equipment in relation to the seam.

2. Method as in cliam 1, using three transducers, one being normally located above the center of the seam, the other two being located alongside of the seam.

3. Method as in claim 1 using two transducers being disposed symmetrical to the center of the seam when in the desired position.

* * * * *